United States Patent [19]

Bokros

[11] Patent Number: 4,689,046
[45] Date of Patent: Aug. 25, 1987

[54] HEART VALVE PROSTHESIS
[75] Inventor: Jack Bokros, Austin, Tex.
[73] Assignee: CarboMedics, Inc., Austin, Tex.
[21] Appl. No.: 710,114
[22] Filed: Mar. 11, 1985
[51] Int. Cl.$^4$ .............................................. A61F 2/24
[52] U.S. Cl. ....................................................... 623/2
[58] Field of Search ................................. 3/1.5; 623/2
[56] References Cited

U.S. PATENT DOCUMENTS 4,254,508  3/1981  Bokros ..................................... 3/1.5
4,276,658  7/1981  Hanson et al. ............................ 3/1.5

Primary Examiner—Richard J. Apley
Assistant Examiner—James Prizant
Attorney, Agent, or Firm—James T. FitzGibbon; Angelo J. Bufalino

[57] ABSTRACT

A heart valve prosthesis with an annular body portion and at least one valve leaflet moveable between open, closed, and intermediate positions. The body includes leaflet ear support formations, each with a contoured recess having spaced apart, tapered arcuate guide wall surfaces and spaced apart convex ear support surfaces. Each valve leaflet includes mounting ears with upper and lower support surfaces of generally trapezoidal outline, a generally flat end face portion, and two spaced apart guide surface portions tapered so as to lie in closely spaced apart relation to the tapered guide walls in the recess.

5 Claims, 11 Drawing Figures

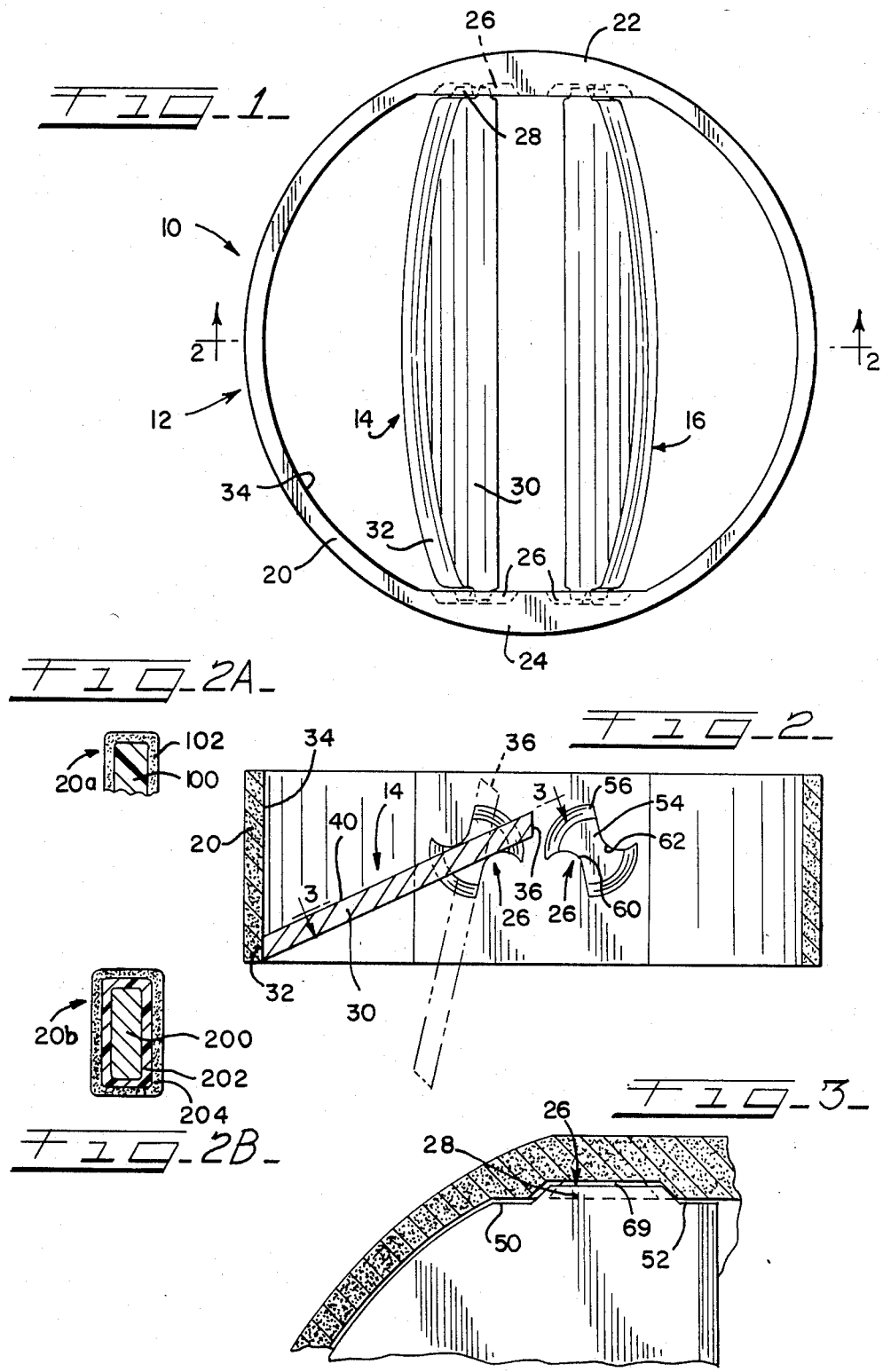

FIG_5
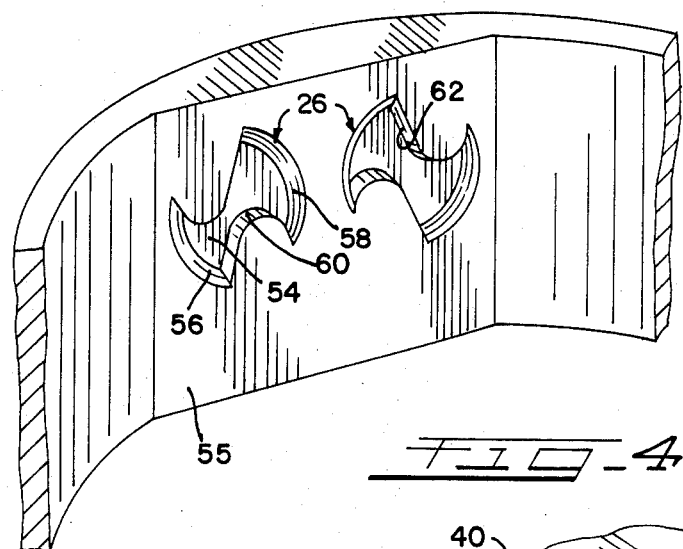
FIG_4
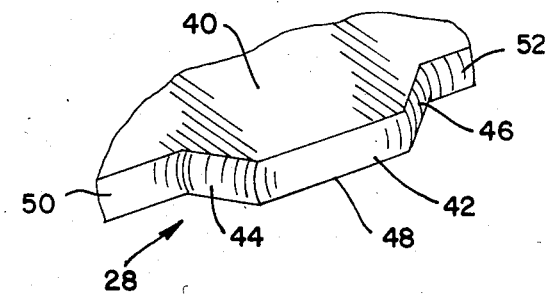
FIG_6
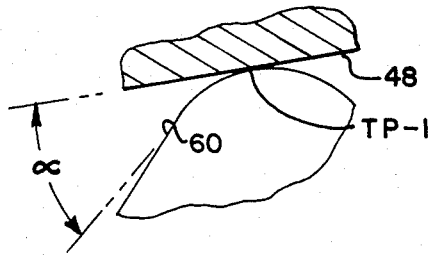
FIG_7
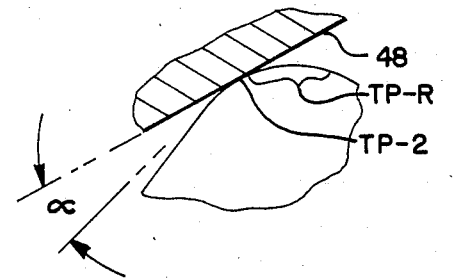

HEART VALVE PROSTHESIS

BACKGROUND OF THE INVENTION

The present invention relates generally to human or animal heart valves, and more particularly, to a heart valve prosthesis suitable for use in humans and adapted to provide more reliable service in use than prior art counterpart valves.

A typical artificial heart valve assembly of an accepted type includes a main body member of annular form, means for securing this body in a desired position within the heart, and one or more valves adapted to control flow of blood through this passageway. While the typical prior art valve assemblies have included ball check type valves, and disc or reed type valves, the most commonly accepted valve used today is the so-called leaflet type valve.

In such constructions, two leaflets are normally preferred and are disposed in opposed or mirror image relation. In the closed position, each valve leaflet occludes or covers half of the opening, with each leaflet being roughly semi-circular in shape and having a rounded exterior margin and an edge portion which engages an inner surface of the main body to provide a peripheral seal, and an inner, diametrically extending edge and adjacent margins adapted to abut the counterpart edges and margins on the second leaflet. Each leaflet is positioned for a rocking or pivoting movement about an axis extending parallel to its interior transversely extending edge surface and offset slightly therefrom.

In use, as blood pressure rises in response to heart contraction or systole, the leaflets are pivoted from a closed position to an open position to permit blood to flow past the leaflets, whereas when the heart contraction is complete, blood tends to flow in the opposite direction in response to the pressure in the aorta, causing the leaflets to close and maintain a pressure in the arterial system. The valve thus operates in the same manner as would be the case with a normal human heart valve.

A number of significant improvements have been made in heart valves, some of the most significant being improvements in materials, including the improvement which comprises coating all exterior surfaces of the prosthesis with pyrolytic carbon. A typical method of coating pyrolytic carbon onto a valve substrate is disclosed in U.S. Pat. No. 3,526,005. This provides very hard surfaces for the components to reduce wear, and provides some insurance against formation of an adhesion of clots to such surfaces.

In spite of significant advances which have taken place in the construction of heart valves, however, there is still room for significant improvement in the area of what may be termed operational reliability.

As is well known, even properly functioning mechanical devices are subject to eventual wear in use. Where the wearing is of a type which may lead to improper functioning or catastrophic failure during a time less than the anticipated life span of a patient, in the case of heart valves, such design is considered as being at least potentially unsatisfactory. Consequently, studies of the durability and reliability of heart valves have been undertaken, and these indicate the potential for further design improvement.

Where the wearing of movable parts is confined in a single, known location, it is anticipated that failure may occur in this location well before it would occur elsewhere in the device. With the now widely accepted simplified single or double leaflet type of heart valve just described, there are only one or two moving parts, and these move with respect to a single, fixed element.

The most widely accepted type of heart valve presently mounts its leaflets for pivoting movement by means of rounded ears extending radially outwardly from sidewalls of the leaflets in an area spaced just apart from the diametrically extending surfaces of the leaflet. These ears are received within guideways which are in the form of contoured grooves extending radially into the main valve body which, as described above, is a generally cylindrical or annular body. The guide surfaces or recesses are complementary in one respect to the shape of the ears. In the prior art, these have been formed as surfaces of at least partial revolution of circular or nearly circular arcuate surfaces. In other words, where the ear is formed as a portion of a circle having a given radius, the counterpart recess is formed as a surface having a slightly greater radius. With corresponding recesses formed in opposed sides of the valve body, and counterpart ears formed on opposite sides of the leaflets, the leaflet, when installed, pivots about the axis formed by these curvilinear, usually partially spherical surfaces.

The surfaces are precisely machined so as to provide a small but definite working clearance for the pivoting parts. When manufactured, the body is deformed or distended so that the ears may be inserted, and each unit so manufactured is then lab tested "dry" to ensure that the leaflets are held tightly enough to be secure against falling free from the prosthesis, but are not so tightly engaged so as to create a binding or restricted valve action.

In the use of this design, and other known designs, a significant potential problem has arisen. This problem has been the concentration of wear in certain areas so that the overall wear is not distributed evenly. In other words, while it had been anticipated that the wear on rounded or spherical ear surfaces and their associated recesses would be minimal, it has been discovered that instead, because of the large amount of play that can occur in the direction of the leaflet chord when the leaflet closes, wear is caused as the leaflet slides relative to the pivot line; the radially curved ear and recessed formations undergo localized wear because of this type of "slop" or sideplay clearance which can cause increased wear in the region where the pivot slides along the ear. This is a function of the degree of play, and is most pronounced when components at the extremes of the tolerance limits are used in a valve. Pivot point play also causes wear where a pivot point supports an ear surface of the leaflet.

As a result of this enhanced wear, while perhaps minimal by some standards, the motion sequence of the valve leaflets becomes less well defined, which in turn causes their motion to be characterized by excess play with respect to the pivot axes, enhancing the potential for binding and/or becoming released into the heart. This results in erratic performance on the one hand, usually manifested in asynchronous closure, or catastrophic failure, such as leaflet release or jamming, on the other hand.

The problem with the best known existing designs, therefore, has been one of an inability to precisely adjust the play and minimize it so malfunctions caused by improper fit-up do not occur. In this connection, it will be appreciated that since each unit is tested individually, manufacturing tolerances are sufficiently accurate to create whatever reliability potential may be achieved with the design. However, with localized rather than distributed wear occuring in existing designs, a difficulty has been created which is impractical to cure by imposing tighter manufacturing tolerances or different fit-up practices. The inherent inability to adjust and control the "slop" in the valves with circular tabs is considered a significant design defect.

In this connection, while prior art heart valves are reliable, and in many cases have been shown on the average to have a projected life expectancy exceeding that of the patient, these figures are statisical and therefore raise the possibility that there may be some erratic function or premature failures caused by extremes of free play in valve fit-up at the extremes of the allowable tolerance. An example is the asynchronous closure of certain prior art leaflet valves, for example.

Moreover, since it is almost always human lives which are being dealt with, there is a definite need for a prosthesis which will not just meet, but which will substantially exceed projected reliability and performance requirements.

In view of the need for further improvement of a heart valve prostheses, it is therefore an object of the present invention to provide an improved heart valve having a novel construction, including a novel method of forming a pivotable connection between the valve leaflets and the valve body.

Another object of the invention is to provide a heart valve having a pair of leaflets each received within a generallly cylindrical valve body, with each leaflet including an oppositely disposed pair of mounting ears of a particular geometric form and arranged for reception within counterpart recesses of complementary form.

Yet another object of the present invention is to provide a novel combination of mounting ear and recess formation adapted for use in single or double leaflet heart valves and adapted to provide greater reliability in use and generally improved functioning.

A further object of the invention is to provide a heart valve construction which enables the valve to be made from synthetic materials and entirely of or coated with pyrolytic carbon, and which is also able to provide a carefully controlled pivoting action as well as one in which whatever wear does occur will not be detrimental to the operation of the leaflets.

Another object of the invention is to provide a heart valve prosthesis which has the advantages of prior art heart valves, but which is free from the drawback of potential lack of reliability and reproducible function associated with such prior art valves.

Yet another object of the invention is to provide a heart valve leaflet which is of a generally semicircular form, and which includes opposed pivot or mounting ears formed on chordal portions of the valve leaflet lying at or near either end of its circular sidewall portions, with each of the ears, in plan view, being of a generally trapezoidal form, and having edges formed as parts of a frusto-conical surface.

The foregoing and other objects and advantages of the invention are achieved in practice by providing a heart valve having a cylindrical main body portion with valve mounting means lying on an inner surface of the body, with the body further defining a central passage for the flow of blood, and including at least one leaflet adapted to move between a closed position occluding blood flow therethrough and open position permitting blood flow therethrough, and being pivoted about an axis of movement which extends along a generally straight line transverse to the cylindrical axis of the body, and with the leaflet including mounting pivot ears of generally trapezoidal plan form. The leaflet mounting recesses are of a particular size and shape to provide improved functioning in use.

The exact manner in which the foregoing and other objects and advantages of the invention are achieved in practice will become more clearly apparent when reference is made to the following detailed description of the preferred embodiments of the invention set forth by way of example and shown in the accompanying drawings, wherein like reference numbers indicate corresponding parts throughout.

BRIEF DESCRIPTION OF THE DRAWINGS

FIG. 1 is a top plan view of a heart valve made according to the invention and embodying certain of its characteristic design features;

FIG. 2 is a vertical sectional view, taken along lines 2—2 of FIG. 1, and showing the heart valve of the invention with one leaflet removed, and the other leaflet in a closed position in solid lines, and in the open position in phantom lines;

FIG. 2A is a fragmentary sectional view, on an enlarged scale, of a heart valve with a modified main body structure;

FIG. 2B is a fragmentary sectional view, on an enlarged scale, of a heart valve with a further modified main body structure;

FIG. 3 is an enlarged fragmentary sectional view taken along lines 3—3 of FIG. 2 and showing a part of the construction of the mounting ear and its associated recess;

FIG. 4 is an enlarged fragmentary perspective view showing a leaflet ear;

FIG. 5 is a fragmentary enlarged perspective view of a recess adapted to receive and position the form of ear shown in FIG. 4;

FIG. 6 is a schematic view showing details of the rockiing movement of the leaflet mounting ear in a given position;

FIG. 7 is a schematic view showing the recess and ear of FIG. 6 in another position thereon;

DESCRIPTION OF THE PREFERRED EMBODIMENTS OF THE INVENTION

Figure 8:
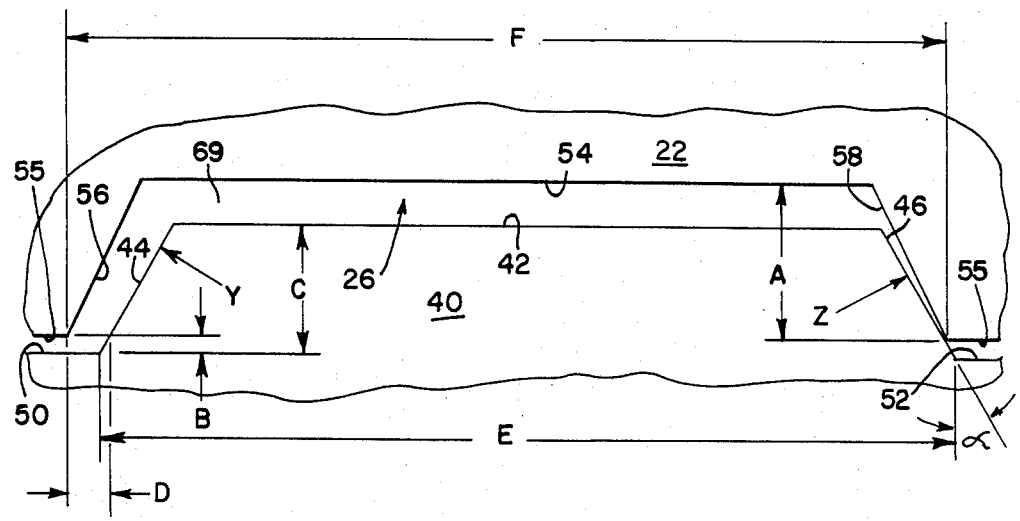
FIG. 8 is a diagramatic view of certain constructional features of the ear and recess parts of the valve of the invention.

While it will be understood that the present invention may be embodied in heart valves having one or two leaflets, or conceivably three or more leaflets, a detailed description will be given of a preferred form of valve wherein there are two leaflets which swing between open and closed positions, and which leaflets have their inner diametral side walls substantially abutting each other in the closed position of the valve and with the ears forming portions of the pivot mechanisms being offset slightly away from these edges.

Referring now to the drawings in greater detail, Fig. 1 shows a heart valve prosthesis generally designated 10 and shown to include three major components, a body generally designated 12 and first and second leaflets generally designated 14, 16. The valve assembly 10 has a plane of symmetry extending through its midsection and generally vertically as shown in FIGS. 1 and 2.

The body 10 is shown to include a generally continuous, circular sidewall portion 20 having a pair of oppositely disposed formations 22, 24 of increased thickness and in which adjacent pairs of recesses 26 are formed. Each of the recesses 26 receive an associated ear 28 on the end portion of a valve leaflet 14, 16. The recesses 26, act as seats for the ears 28 of the leaflets 14, 16 and since the recesses 26, ears 28, and leaflets 14, 16 are all substantially identical to their counterpart, only one of each will be described in detail.

The left hand leaflet 14 is shown to include a principal leaflet body portion 30 having a curvilinear exterior edge 32 which is bevelled so as to form a fluid-tight fit with a radially inwardly directed surface 34 on the curvilinear portion of valve body 20. The leaflet 14 also contains a bevelled, generally planar center edge surface 36 adapted, in the closed position of the leaflet 14 to mate with a counterpart surface (not shown in detail) on the adjacent leaflet 16. The surface 36 extends transversely to the cylindrical axis of the valve body 12.

Mounting of the valve ears, which is an important feature of the invention, is achieved by a combination of three important features, one being the provision of the ear 28 for example, on the leaflet 14. This ear 28 is best shown in FIG. 4 to include a top surface portion 40 of generally trapezoidal shape when shown in plan view and being defined by an outermost, vertically extending end surface 42 and opposed diagonally extending, contoured surfaces 44, 46. These surfaces 44, 46 are frustoconical surfaces of revolution about the axis of pivoting movement of the leaflets 14, 16 and extend between the top ear surface 40 and the bottom ear surface 48.

As shown, the surfaces 44, 46 would be truly frustoconical if the product of full revolution, but, being surfaces of only partial revolution, subtend only a slight angle rather than a full 360 degree angle.

The leaflet ears, such as the ear 28, according to the invention, are received in use within one of the plurality of contoured valve ear seating recesses 26, a description of only one of which is believed necessary to an understanding of the invention. Thus, referring again to one of such recess 26, as shown in FIG. 5, this element includes a flat end wall or endface surface 54, a pair of opposed, truncated frustoconical or bevelled sidewall surfaces 56, 58 and horizontally extending rounded ear support or seating surfaces 60, 62.

Functionally speaking, the end face surface 54 may be that as an end play limiting surface, the opposed bevelled side wall surfaces 56, 58 as guide surfaces which determine the arcuate movement of the ears 28, while the support or seating surfaces 60, 62 may be considered leaflet ear supports, it being understood that the support is support against dynamic ear movement caused by blood flow rather than support against movement in response to gravity only.

Likewise, from the functional standpoint, the ear surfaces 44, 46 act as guide surfaces, the top and bottom ear surfaces 40, 48 as support surfaces, and the end face surface 42 as an end play limiting surface.

In the operation of the assembled valve 10, each of the leaflets 14, 16 is supported from time to time by various surfaces as it operates. Thus, the rounded seat surface 60 extends horizontally and faces upwardly to support the opposibly facing lower ear surface 48 when there is an overall downward force acting on the leaflet. As the leaflet swings to an open position, it continues to rest on a portion of the support surface 60, and is guided in its arcuate path as it opens pivotally by contact, interference, or near-contact between the frustoconical surfaces 44, 46 for example, on the ear 28 and the counterpart tapered or bevelled surfaces 56, 58 forming parts of the recess 26.

When the valve leaflet 14 is fully closed and is acted upon by a net pressure coming from the downstream side or from beneath the valve as shown in FIG. 2, resistance to axial displacement is provided by engagement between a part of the downwardly directed ear seat surface 62 and the upwardly directed surface 40 on the valve leaflet ear 28. This movement involves a rolling pivot action between the surfaces 40 and 62 rather than a rocking action over a sngle pivot point. Endplay is restricted within permissible limits by engagement of the respective end wall surfaces 42 on the ear 28 and the bottom or end face surface 54 of the well or recess 26, as was the case in valve opening. Sideplay is restricted by engagement of the ear surfaces 44, 46 and the recess tapered surfaces 56, 58 as well.

Consequently, in use, when there is a pressure from above, as in FIG. 2, the left hand valve leaflet 14 tends to open, inasmuch as a greater portion of its surface area lies to the left of its pivot axis than to the right thereof. In opening, the valve unseats by disengagement of both the cylindrical surfaces 32, 34 and the rectilinear center transverse surfaces 36. During this action, the ear and recess surfaces just described combine to guide the ears 28 and their leaflet 14 through a limited range of arcuate movement. By reference to the phantom line position of the leaflet 14 in FIG. 2, it will be noted that excess leaflet movement is limited by the contour of the recesses, whose surfaces 60, 62 prevent undue opening, while movement beyond desired limits is also prevented by engagement of the bevelled surface 32 and inner leaflet edge 36, with cylinder wall 34 and the inner counterpart edges of the opposing leaflet 16, respectively.

Figure 9:
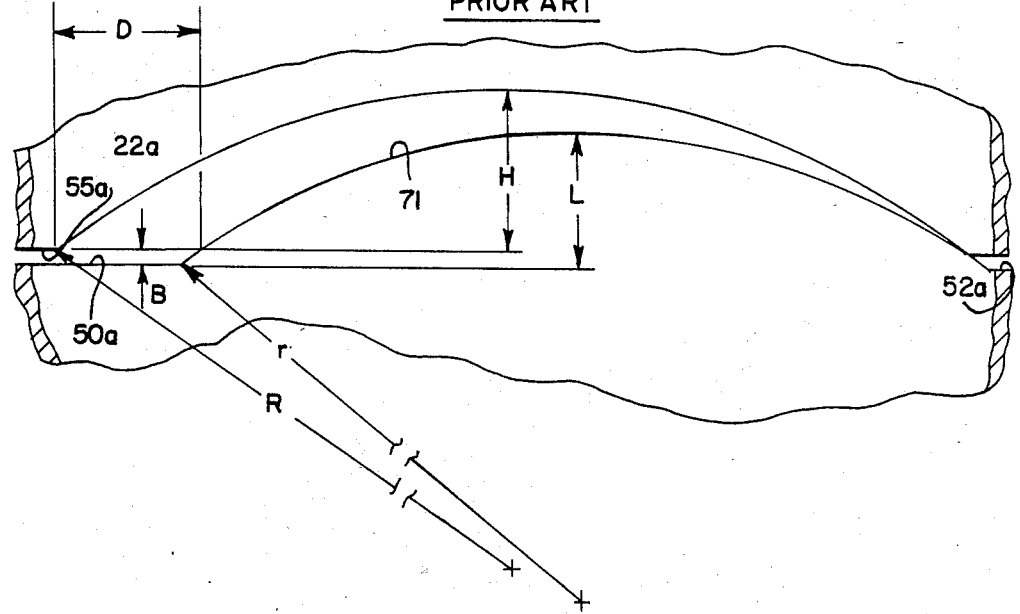
FIG. 9 is a diagramatic view of certain constructional features of a prior art ear and recess and illustrating certain potential shortcomings thereof.

Referring now to FIGS. 8 and 9, the significance of one aspect of the novel trapezoidal ear geometry may be seen. These figures contrast the construction of the ears of the present invention (FIG. 8) with that of the prior art (FIG. 9).

Briefly stated, prior art practice suggested the formation of ears having a partially spherical sector exterior surface 71 of a certain radius r. In order to provide for working clearance, a recess of depth H was provided in the recess housing 22a, such recess being formed on a radius R. When a certain amount of endplay is specified or permitted, arising from the difference in recess depth H and ear height L providing a working clearance, at least in the initial use, equal to H minus L, an endplay clearance of D is the result. H is measured with respect to a reference flat surface 55a (FIG. 9) and L with respect to an adjacent leaflet edge surface 50a. The clearance between these surfaces is B in FIG. 9. As will be noted by simple geometry, (as H-L) increases, that is, as the difference between the radii of the leaflet ear edge and the radii of the recess end wall becomes larger, so as to provide sufficient endplay, play D FIG. 9) becomes greater at a greatly increasing rate.

While this is not always apparent in a prosthesis wherein there is an initially proper fit between the ends of the mounting ears and the inner surfaces of the ear-receiving recesses, both surfaces being actually spherical in part, studies of wear patterns in leaflet valves used in life tests have shown a localization of wear causing critical dimensional changes which in turn permit greatly increased end or side play. This can cause the wear to accelerate, since the "slop" is increased. While the wear causing increased endplay may be very slight, a significant increase in sideplay will result. Where the wear has been localized on the surfaces in question, life tests indicate that a potentially hazardous condition may exist. Certainly, valve function can and does change.

According to the present invention, as shown in FIG. 8 the leaflet ears are formed as conic section surfaces which are truncated in perpendicular planes. In the case of the leaflet ears 28, and in the case of the well or recess 26, contoured surfaces, including substantially flat end face surfaces 42 and frustoconical side walls 44, 46 are received in a recess 26 of desired shape. This permits arcuate movement of the valve leaflet through perhaps 40 to 60 degrees, and in a preferred embodiment, 53 degrees, while carefully controlling and limiting endplay and sideplay or misalignment.

As will be noted from FIG. 8, in a well or recess having an entrance diameter F, an ear having a maximum width of E may be inserted and retained. The depth A of the recess is slightly greater than the height C of the ear. Referring to the angles, an included half-angle of the cone frustum $\alpha'$, measured as shown in FIG. 9, is numerically slightly greater than the half angle measured in the same way, of the walls 56, 58 of the recess. With this construction, for any given increase in endplay (A–C), there is only a very slight increase in sideplay D, thus permitting a much more accurate and more satisfactory fit to be made.

In other words, given certain tolerances, in the case of the leaflet ear mounting system of the present invention, not only will wear be decreased, but the wear that does occur will not be creative of greatly "leveraged" increases in undesirable side play, as in prior art constructions. For any increase in endplay, there will be only a correspondingly moderate increase in side play. Thus, the reported propensity of prior art devices to develop asychronous closure may be significantly reduced.

Inasmuch as the leaflets and their mounting ears operate in a fluid medium, a zero clearance or excessively tight clearance is not the solution to a problem of potential valve pivot failure. Likewise, although relatively rigid, the valve body itself "sees" certain pressure fluctuations and is located by a sewing cuff or otherwise in a heart. As such, the valve body itself undergoes very slight deflections in use, for which an allowance must be made by providing some working clearance. Thus, merely decreasing or increasing the existing working clearance is not a proper solution to the problem, inasmuch as one action would create potential binding and the other would create potential leakage and failure.

Consequently, it has been determined that, in at least one preferred form of the invention, the valve body can and should be made from a rigid metal material instead of a less rigid plastic material. Accordingly, there are shown herein both plastic and metal-containing valve bodies.

Thus, referring now to FIG. 2A, there is shown an enlarged fragmentary section of the side wall portion 20a of the valve 10. This shows that the side wall may itself be composed of a structural plastic body 100 having a coating 102 of pyrolytic carbon thereover.

FIG. 2B shows that the body 20b may include a metal inner body 200 of substantial rigidity, and that this body may be coated with a plastic material 202 which in turn includes a pyrolytic carbon covering 204.

These examples illustrate that it may be desirable to use coated materials, including coated metal materials in making the product of the invention. It is believed known to those skilled in the art that the exact material used are not a feature of the invention which is novel per se. Likewise, using present technology, the products are preferably completely coated with pyrolytic carbon, although this is not, per se, necessary to the functioning of the improved design product.

$$D = 2 \times \left\{ \sin\left[ \cos^{-1}\left( \frac{R-H}{R} \right) \right] \times R - \sin\left[ \cos^{-1}\left( \frac{r-h+B}{r} \right) \right] \times r \right\}$$

Another feature of importance is the provision of the rounded ear pivot surfaces 60, 62, for example. As shown and described with respect to FIGS. 6 and 7, as the tangent point TP between the lower ear surface 48 and the upwardly facing recess ear seat surface 60 moves between positions TP-1 (FIG. 6) and TP-2 (FIG. 7), there is a broad range of contact or tangent points TP-R rather than the single tangent or fulcrum pivot point, along which the leaflet is supported.

This "washes" the surface, spreads out the area of contact and, it is believed, diminishes possible red cell damage or crushing, and permits a floating action which extends wear.

While not specifically shown in FIGS. 6 and 7, it will be understood that a similar rolling action or moving of tangent or contact points occurs in respect to the upper ear surface 40 and the lower recess ear support or seat surface 62. The leaflet ears are thus alternately pivoting about and/or being supported by first a lower surface 60 and then an upper surface 62 of the recess 26, which respectively engage downwardly and upwardly directed surfaces 48, 40 on the leaflet ear 28.

The present invention takes advantage of the simplicity of the pivotable leaflet valve action and provides support and facing surfaces in the respective ear-receiving recesses sufficient to control the valve leaflet movant, and to reduce wear by reducint slop and providing a rolling action around a rounded pivot rather than localizing wear.

Moreover, the configuration of a frustoconical pivot action guide surfaces on both the ear and in the recess, with these surfaces being related such that the well or recess is steeper or has an included angle less than that of the ears of the leaflet provides a potential for greatly extended wear and reliability in a highly critical environment.

The foregoing combination of features is believed to provide a greatly improved heart valve prosthesis which tests have indicated will have a greatly extended potential life and incorporate the other functional advantages referred to herein and inherent in the design.

It will thus be seen that the present invention provides a new and improved heart valve prosthesis having a number of advantages and characteristics including those pointed out herein and others which are inherent in the invention.

A description of the present forms of invention having been described by way of example, it is anticipated that variations of the described foms of apparatus may be made without departing from the spirit of the invention and the scope of the appended claims.

I claim:

1. A heart valve prosthesis comprising a valve body portion of annular form having side walls defining a central passage extending axially therethrough, and at least one valve leaflet disposed within said valve body and said passage, said leaflet being and adapted for movement between open, closed, and a range of intermediate positions thereof, said valve prosthesis being characterized in that said body includes at least a pair of spaced apart leaflet ear support formations each having a generally radially inwardly directed outer surface portion, and, lying within said leaflet ear support formation, at least one contoured recess having an inner end face, a pair of spaced apart, tapered, arcuate guide wall surfaces extending between said inwardly directed outer surface portion of said formation and said inner end face thereof, and a pair of spaced apart, curved arcuately convex ear support surfaces joined at their ends to the ends of said guide wall surfaces, said leaflet including a leaflet body portion having top and bottom surface portions and an outer side wall portion extending between and joining portions of said top and bottom surfaces, said outer side wall portion being adapted to cooperate in use with inwardly directed portions of said annular body so as to form a fluid-tight seal therewith in at least one postion of said leaflet, and mounting ears on said leaflet adapted to be received for free but limited movement within said receses, said ears having upper and lower support surfaces of generally trapezoidal outline, a generally flat end face portion, and two spaced apart guide surface portions, said guide surface portion being tapered so as to lie in closely spaced apart relation to said tapered guide walls in said recess.

2. A heart valve as defined in claim 1 wherein said at least one leaflet comprises two leaflets.

3. In a heart valve prosthesis having a generally annular valve body with a central passageway extending axially therethrough, and at least one leaflet disposed within said passageway and positioned for pivotal movement between open and closed positions, and a range of intermediate positions, with said leaflet having an upstream surface and a downstream surface and a side wall surface extending between said upstream and downstream surfaces, with at least portions of said side wall surface being adapted to engage inwardly directed portions of said annular body in substantially fluid-tight relation, said body further including spaced apart recesses for positioning and supporting leaflet ears, and said leaflet including ears adapted to be received within said recess to provide a free but limited movement action for such leaflet, the improvement comprising said ears being of generally trapezoidal configuration in plan and having substantially flat upstream and downstream surface portions, a generally flat end surface portion and a pair of tapered ear side wall portions acting as guide surface portions, said recess including a generally flat end face portion arranged in opposite facing relation to said ear end face surface, tapered recess guide wall surfaces extending between a portion of said valve body and said recess end face surface, said surfaces being of arcuate configuration, said recess further including leaflet support surfaces extending into said recess and joined at their ends to the end portions of said tapered recess guide walls, each of said leaflet support surfaces having an arcuately convex surface portion between its ends, whereby said leaflet moves between said open, closed and intermediate position, said ears rockingly engaged and are supported by a major portion of said convex support surface so as to minimize wear on said ears and said ear support surfaces.

4. A heart valve as defined in claim 3 wherein said at least one leaflet comprises two leaflets.

5. A heart valve prosthesis as defined in claim 3 wherein said taper on said recess is slightly shallower than said taperer on said ear guide surfaces.

* * * * *